United States Patent
Lipman et al.

(10) Patent No.: US 9,993,256 B2
(45) Date of Patent: Jun. 12, 2018

(54) CUSTOMIZED UNICOMPARTMENTAL TIBIAL CUTTING GUIDE

(71) Applicant: Hospital for Special Surgery, New York, NY (US)

(72) Inventors: Joseph D. Lipman, New York, NY (US); Geoffrey H. Westrich, New York, NY (US)

(73) Assignee: Hospital for Special Surgery, New York, NY (US)

( * ) Notice: Subject to any disclaimer, the term of this patent is extended or adjusted under 35 U.S.C. 154(b) by 686 days.

(21) Appl. No.: 14/487,803

(22) Filed: Sep. 16, 2014

(65) Prior Publication Data

US 2015/0088143 A1    Mar. 26, 2015

Related U.S. Application Data

(60) Provisional application No. 61/880,543, filed on Sep. 20, 2013.

(51) Int. Cl.
| A61B 17/15 | (2006.01) |
| A61B 17/17 | (2006.01) |
| A61B 17/56 | (2006.01) |
| A61B 34/10 | (2016.01) |

(52) U.S. Cl.
CPC ........ *A61B 17/1764* (2013.01); *A61B 17/157* (2013.01); *A61B 2017/568* (2013.01); *A61B 2034/108* (2016.02)

(58) Field of Classification Search
CPC .................................................. A61B 17/157
See application file for complete search history.

(56) References Cited

U.S. PATENT DOCUMENTS

| 5,370,692 A | 12/1994 | Fink et al. |
| 8,265,949 B2 | 9/2012 | Haddad |
| 8,323,288 B2 | 12/2012 | Zajac |
| 8,357,166 B2 | 1/2013 | Aram et al. |
| 8,377,068 B2 | 2/2013 | Aker et al. |
| 8,398,645 B2 | 3/2013 | Aker et al. |
| 8,419,740 B2 | 4/2013 | Aram et al. |
| 8,425,523 B2 | 4/2013 | Aram et al. |
| 8,425,524 B2 | 4/2013 | Aker et al. |
| 8,538,570 B2 | 9/2013 | Stanhope et al. |
| 8,594,395 B2 | 11/2013 | Roose et al. |
| 8,617,170 B2 | 12/2013 | Ashby et al. |

(Continued)

*Primary Examiner* — Andrew Yang
(74) *Attorney, Agent, or Firm* — Kim Winston LLP

(57) ABSTRACT

A customized unicompartmental tibial cutting guide for orthopedic surgery is provided. The tibial cutting guide includes a first mating surface having a customized patient-specific negative contour to match a corresponding contour of an anterior region of a tibia of a patient and a second mating surface extending transverse to the first mating surface to a midpoint of a tibial plateau of a medial or lateral condyle of the tibia. The second mating surface includes a customized patient-specific negative contour to match a corresponding contour of a mid-region of the tibial plateau of the medial or lateral condyle. The second mating surface is limited to a region between an intercondyloid eminence and a lateral or medial edge of the tibial plateau. The tibial cutting guide also includes a first cutting guide surface and a second cutting guide surface positioned transverse to the first cutting guide surface.

20 Claims, 8 Drawing Sheets

(56) References Cited

U.S. PATENT DOCUMENTS

| | | |
|---|---|---|
| 8,617,175 B2 | 12/2013 | Park et al. |
| 8,641,721 B2 | 2/2014 | Aram et al. |
| 8,777,946 B2 | 7/2014 | Lindahl et al. |
| 9,402,637 B2 * | 8/2016 | Song .................. A61B 17/1764 |
| 9,486,226 B2 * | 11/2016 | Chao ................... A61B 17/157 |

* cited by examiner

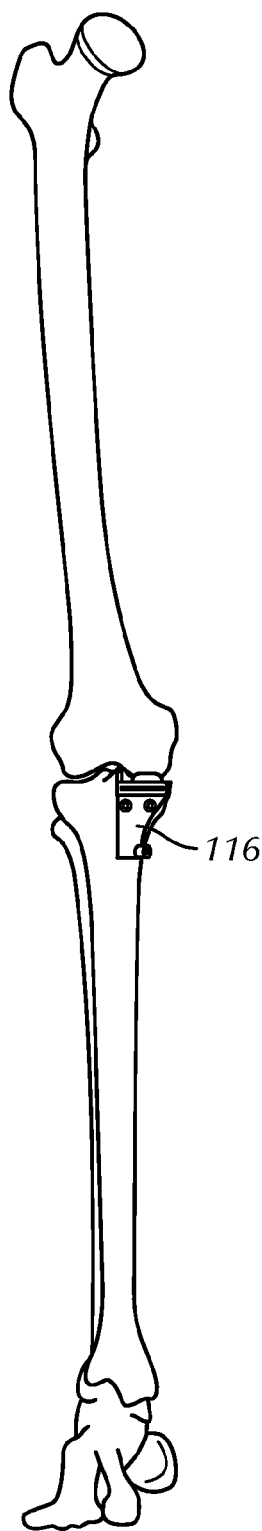
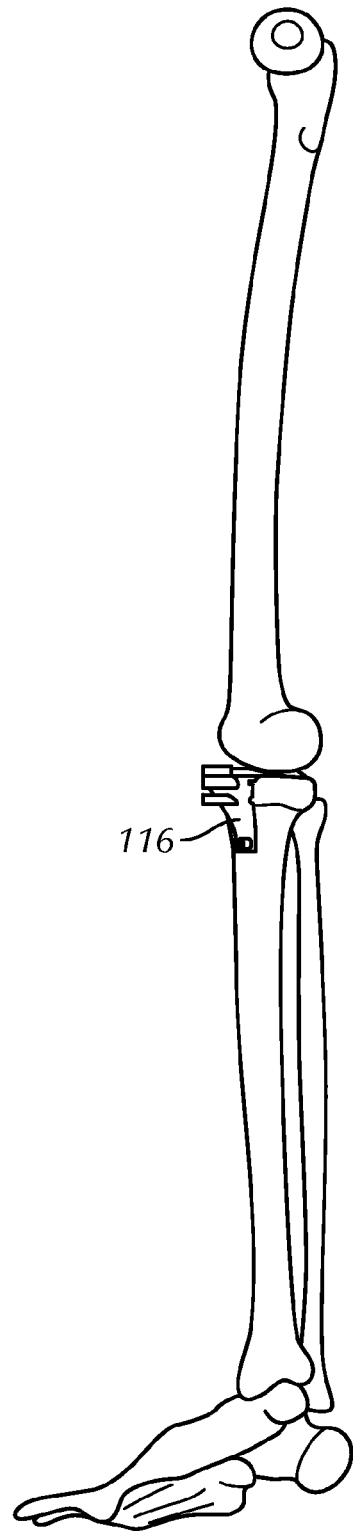
*FIG. 13*  *FIG. 14*

CUSTOMIZED UNICOMPARTMENTAL TIBIAL CUTTING GUIDE

CROSS-REFERENCE TO RELATED APPLICATIONS

This application claims the benefit of U.S. Provisional Application No. 61/880,543, filed Sep. 20, 2013, the entire disclosure of which is incorporated by reference herein in its entirety.

BACKGROUND OF THE INVENTION

The present invention relates generally to orthopedic surgical instruments. In particular, the present invention relates to a customized unicompartmental tibial cutting guide.

Unicompartmental knee arthroplasty (UKA) has significantly increased its market share in the treatment of unicompartmental osteoarthritis in the United States over the last decade. Long-term survival of UKA in registries has, however, been reported to be inferior to that of total knee arthroplasty (TKA). Experience with UKA contributes tremendously to successful outcome of this procedure. As indications for UKA are less common, this experience is relatively hard to achieve in the average orthopedic practice.

Many of the early revisions of UKA seem to be due to implant-related problems, such as malpositioning, and this may at least in some cases relate to the experience level of the operating surgeon. Thus, an easy and affordable approach for reproducible implantation of UKA components would be highly desirable. This is accomplished by the patient-specific instrumentation (PSI) of the present invention applying customized unicompartamental tibial cutting guides for orthopedic surgery.

BRIEF SUMMARY OF THE INVENTION

In accordance with a preferred embodiment, the present invention provides a customized unicompartmental tibial cutting guide for orthopedic surgery comprising a first mating surface, a second mating surface, a first cutting guide surface, and a second cutting guide surface. The first mating surface including a customized patient-specific negative contour to match a corresponding contour of an anterior region of a tibia of the patient. The second mating surface extending substantially transverse to the first mating surface to about a midpoint of a tibial plateau of a medial condyle or a lateral condyle of the tibia. The second mating surface also includes a customized patient-specific negative contour to match a corresponding contour of a mid-region of one of the tibial plateau of the medial condyle or the tibial plateau of the lateral condyle. The second mating surface is limited to a region between an intercondyloid eminence and a lateral or a medial edge of the tibial plateau. The first cutting guide surface is positioned distal to the second mating surface. The second cutting guide surface is positioned substantially transverse to the first cutting guide surface and adjacent a medial side of the first mating surface.

In accordance with another preferred embodiment, the present invention provides a customized unicompartmental tibial cutting guide for orthopedic surgery comprising a mating surface, a first cutting guide surface, and a second cutting guide surface. The mating surface including a customized patient-specific negative contour to match a corresponding contour of a tibia of the patient extending continuously from a tibial plateau of a medial condyle or a lateral condyle of the tibia to an anterior region of the tibia. The mating surface has a first portion extending along the anterior region of the tibia and continuously to a second portion extending substantially transverse to the first portion to about a midpoint of the tibial plateau of the medial condyle or the lateral condyle of the tibia. The second portion is limited to a region between an intercondyloid eminence and a lateral or a medial edge of the tibial plateau. The first cutting guide surface is positioned distal to the second portion. The second cutting guide surface is positioned substantially transverse to the first cutting guide surface and adjacent a medial side of the customized unicompartmental tibial cutting guide.

In accordance with yet another preferred embodiment, the present invention provides a customized unicompartmental tibial cutting guide for orthopedic surgery comprising a cutting block and a tongue releasably attachable to the cutting block. The cutting block includes a first surface for engagement with an anterior region of a tibia, and a first cutting guide surface extending completely across the cutting block. The tongue includes a mating surface having a customized patient-specific negative contour to match a corresponding contour of a mid-region of one of a tibial plateau of a medial condyle or a tibial plateau of a lateral condyle of a tibia of the patient.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 13 is a front elevation view of the customized unicompartmental tibial cutting guide of FIG. 2 attached to a patient's leg at full extension;

FIG. 14 is a medial side elevation view of the customized unicompartmental tibial cutting guide of FIG. 2 attached to a patient's leg at full extension;

DETAILED DESCRIPTION OF THE INVENTION

Reference will now be made in detail to the preferred embodiments of the invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. Such directional terms used in conjunction with the following description of the drawings should not be construed to limit the scope of the invention in any manner not explicitly set forth. Additionally, the term "a," as used in the specification, means "at least one." The terminology includes the words above specifically mentioned, derivatives thereof, and words of similar import.

Figure 1:
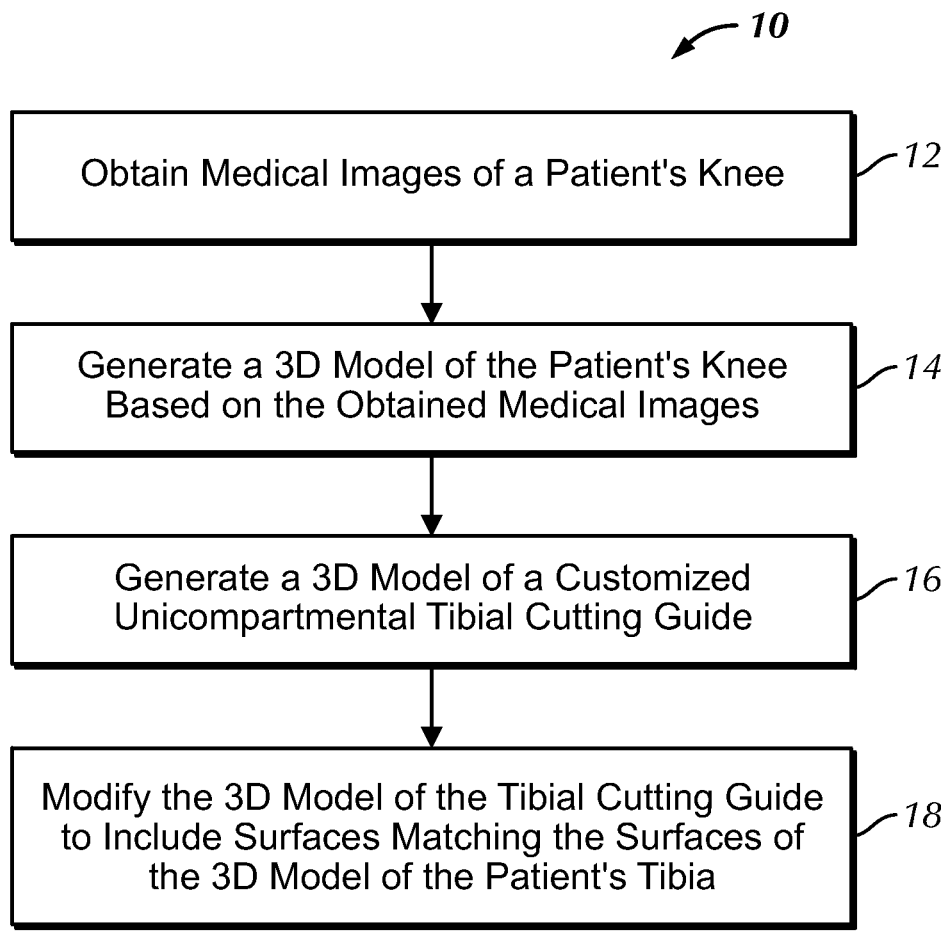
FIG. 1 is a simplified flow diagram of a method of designing and fabricating a customized unicompartmental tibial cutting guide in accordance with a preferred embodiment of the present invention.

Referring to FIG. 1, an algorithm 10 for fabricating a customized patient-specific orthopaedic surgical instrument is illustrated. What is meant herein by the term "customized patient-specific orthopaedic surgical instrument" is a surgical tool for use by a surgeon in performing an orthopaedic surgical procedure that is intended, and configured, for use on a particular patient. As such, it should be appreciated that, as used herein, the term "customized patient-specific orthopaedic surgical instrument" is distinct from standard, non-patient specific orthopaedic surgical instruments that are intended for use on a variety of different patients. Additionally, it should be appreciated that, as used herein, the term "customized patient-specific orthopaedic surgical instrument" is distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic prostheses.

In accordance with the embodiments of the present invention, the customized patient-specific orthopaedic surgical instrument is customized to the particular patient based on the location at which the instrument is to be coupled e.g., the tibia. For example, in some embodiments, the customized patient-specific orthopaedic surgical instrument may include a bone-contacting or facing surface having a negative contour that matches or substantially matches the contours of an anterior portion of the tibia of the patient. As such, the customized patient-specific orthopaedic surgical instrument is configured to be coupled to the tibia bone of a patient at that particular location on the patient's bone. That is, the negative contour of the bone-contacting surface is configured to receive the matching contour surface of the portion of the patient's bone, similar to a jigsaw puzzle. As such, the orthopaedic surgeon's guesswork and/or intra-operative decision-making with respect to the placement of the orthopaedic surgical instrument are reduced.

For example, the orthopaedic surgeon may not be required to locate landmarks on the patient's tibia bone to facilitate the placement of the orthopaedic surgical instrument, which typically requires some amount of estimation on part of the surgeon. Rather, the orthopaedic surgeon may simply couple the customized patient-specific orthopaedic surgical instrument on the bone of the patient in the unique location. When so coupled, the cutting plane, drilling holes, milling holes, and/or other guides are defined in the proper location relative to the bone and intended orthopaedic prosthesis. The customized patient-specific orthopaedic surgical instrument may be embodied as any type of orthopaedic surgical instrument such as, for example, a bone-cutting block, a drilling guide, a milling guide, or other type of orthopaedic surgical instrument configured to be coupled to a bone of a patient.

The process for manufacturing the customized unicompartmental tibial cutting guide 100 includes obtaining medical images of a patient's knee (step 12) e.g., using computed tomography (CT) to generate three-dimensional (3D) models of the patient's leg, including the patient's knee joint i.e., tibia, femur and fibula, based on the obtained medical images (step 14). The 3D models of the patient's leg can be in the form of a stereolithography file format i.e., a .stl file format.

Once the 3D model of the patient's tibia is created, an optimal position for implantation of a tibial implant on the tibia is determined. This determined position of the tibial implant is then used to determine a position the tibial cutting guide is to be attached to the tibia in order properly resect the tibia for receiving the tibial implant.

Thereafter, a 3D model of a unicompartmental tibial cutting guide is generated (step 16) and then customized using the 3D model of the patient's leg. The foregoing 3D models can be generated using conventional computer-aided design software systems. The surfaces of the unicompartmental tibial cutting guide are customized by matching it to the contours of the patient's bones (step 18) e.g., using a Boolean operation to create the surface on the tibial guide that matches the patient's bone, at the determined position of attachment of the tibial cutting guide to the patient's tibia. The foregoing method of producing the customized unicompartmental tibial cutting guide is preferred however, the other methods of manufacturing a customized unicompartmental tibia cutting guide include those as disclosed in U.S. Pat. Nos. 8,377,068; 8,419,740 and 8,617,175, the entire disclosures of which are incorporated by reference herein.

For purposes of illustration and not by way of limitation, preferred embodiments of present invention will be hereinafter described in reference to a medial customized unicompartmental tibial cutting guide. However, the present invention is equally applicable to a lateral customized unicompartmental tibial cutting guide, which may be configured similar to a mirror image of the medial customized unicompartmental tibial cutting guide. In other words, the present invention is suitable for a unicompartmental tibial cutting guide for either a medial or lateral UKA.

Figure 4:
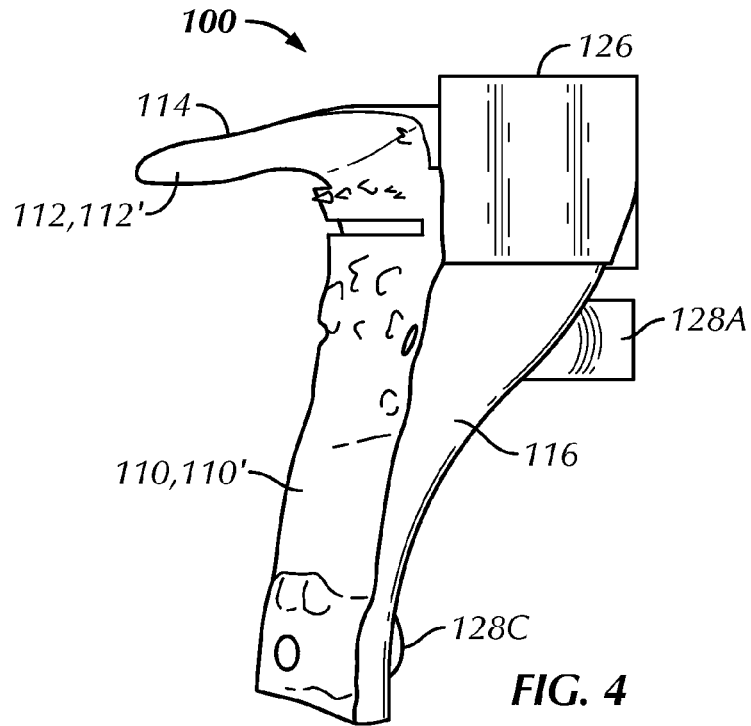
FIG. 4 is a medial side elevation view of the customized unicompartmental tibial cutting guide of FIG. 2.

Referring to FIG. 4, the customized unicompartmental tibial cutting guide 100 is "customized" in that it is designed to have a first matching surface 110 that is a negative contour that matches a corresponding contour of an anterior region of the patient's tibia. In other words, the first mating surface 110 includes a customized patient-specific negative contour to match a corresponding contour of an anterior region of a tibia of the patient. In general, the tibial cutting guide is configured to fit along the antero-medial aspect of the tibia. In a preferred aspect, the tibial cutting guide can have a length ranging from about 30 to 54 mm, but can alternatively be more or less depending on the particular anatomy of the patient.

Figure 11:
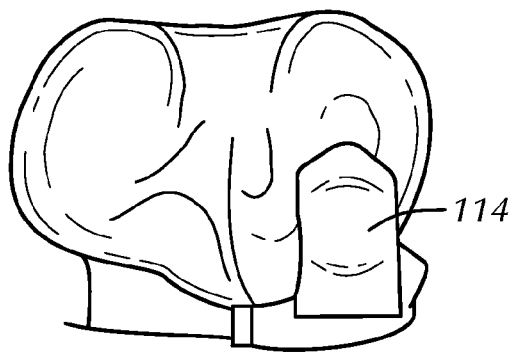
FIG. 11 is a top plan view of the customized unicompartmental tibial cutting guide of FIG. 2 attached to a tibia.
Figure 12:
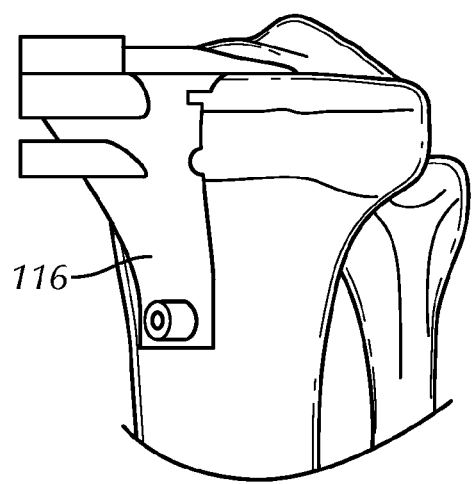
FIG. 12 is medial side elevation view of the customized unicompartmental tibial cutting guide of FIG. 2 attached to a tibia.

The tibia cutting guide 100 also includes a second mating surface 112 extending substantially transverse to the first mating surface 110 to about a midpoint of a tibial plateau of a medial condyle or a lateral condyle of the tibia (see FIG. 11). Preferably, the second mating surface 112 extends to and terminates a lowest position of the tibial plateau. As a result of terminating at the lowest position of the tibial plateau, the second mating surface in combination with the first mating surface functions in a clamp-like manner. The second mating surface 112 includes a customized patient-specific negative contour to match a corresponding contour of a mid-region of one of the tibial plateau of the medial condyle or the tibial plateau of the lateral condyle. This precision matching of the second mating surface 112 allows for proper placement of the tibial cutting guide 100 in the anterior-posterior, medial-lateral, and proximal distal directions.

The second mating surface 112 is formed on an underside of a tongue 114 extending from a main body 116 of the tibial cutting guide 100. The tongue 114 extends posteriorly from the main body 116 a distance sufficient to reach a midpoint of the tibial plateau of the medial condyle or the lateral condyle of the tibia. Preferably, the tongue extends sufficiently posteriorly to reach and terminate at a lowest position of the tibial plateau. As a result of terminating at the lowest position of the tibial plateau, the tongue in combination with the remainder of the tibial cutting guide functions in a clamp-like manner. The width of the tongue is narrower than the main body 116 and sized to be situated between the intercondyloid eminence and a lateral or medial edge of tibial plateau (see FIG. 11). As such, the second mating surface 112 is limited to a region between the intercondyloid eminence and one of the lateral or medial edge of the tibial plateau.

Figure 5:
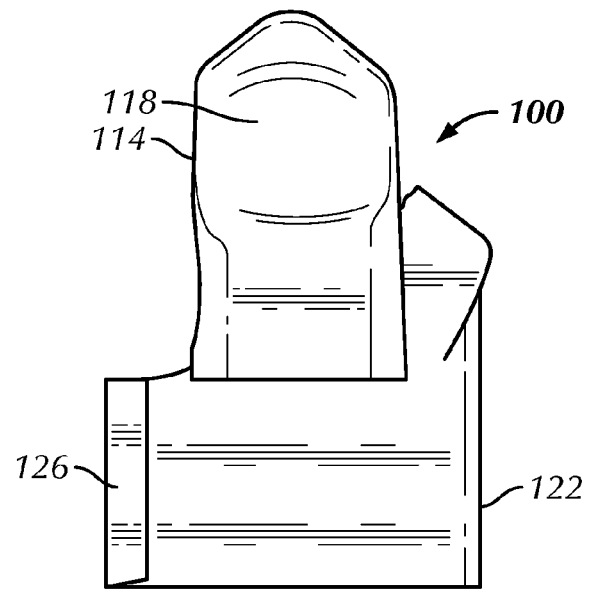
FIG. 5 is a top plan view of the customized unicompartmental tibial cutting guide of FIG. 2.
Figure 6:
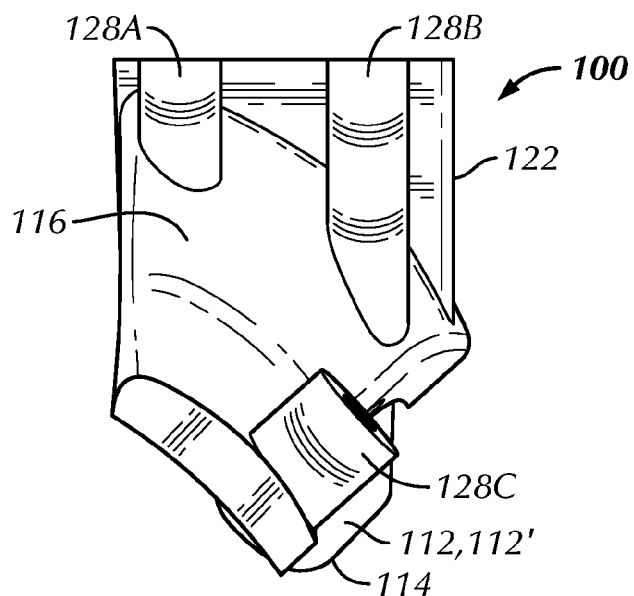
FIG. 6 is a bottom plan view of the customized unicompartmental tibial cutting guide of FIG. 2.
Figure 7:
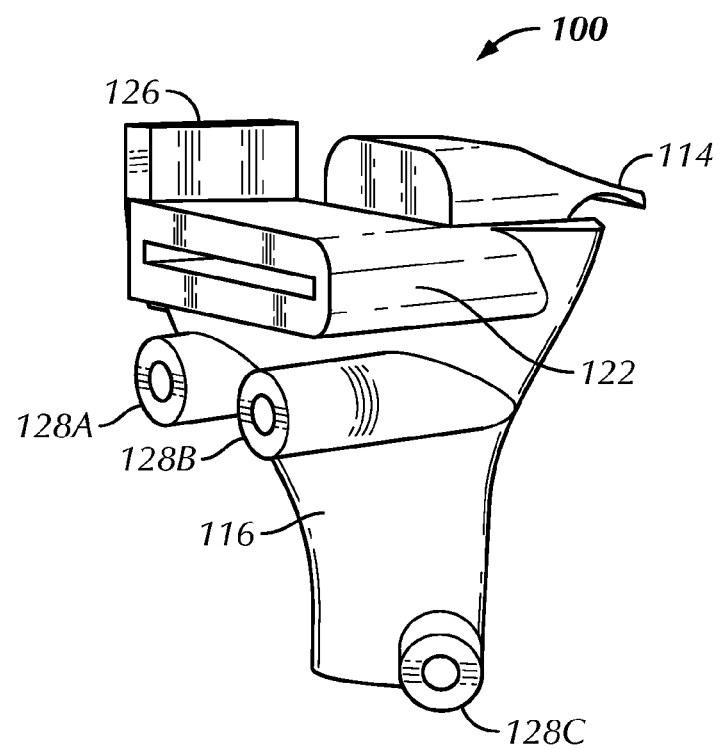
FIG. 7 is a front perspective view of the customized unicompartmental tibial cutting guide of FIG. 2.
Figure 8:
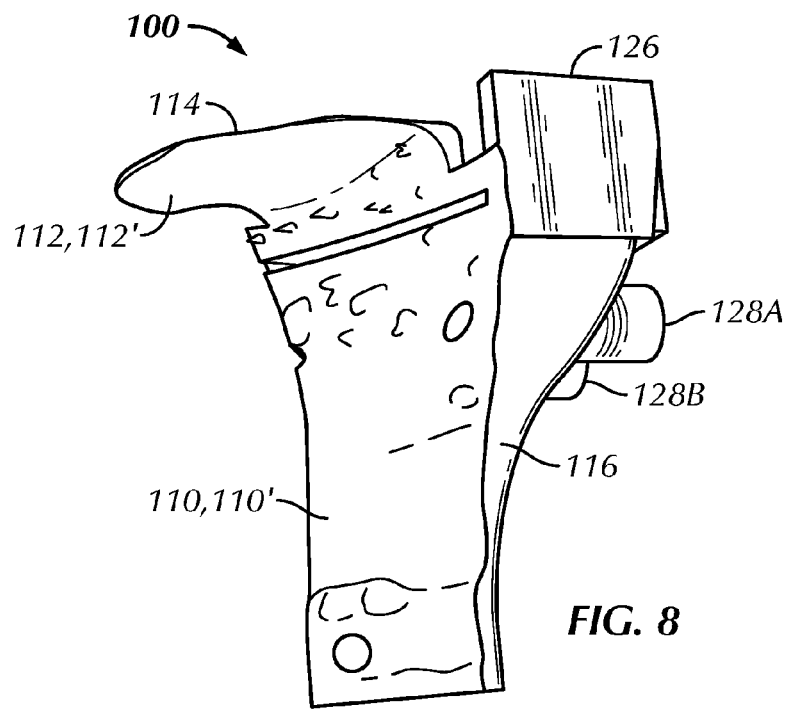
FIG. 8 is a rear perspective view of the customized unicompartmental tibial cutting guide of FIG. 2.
Figure 9:
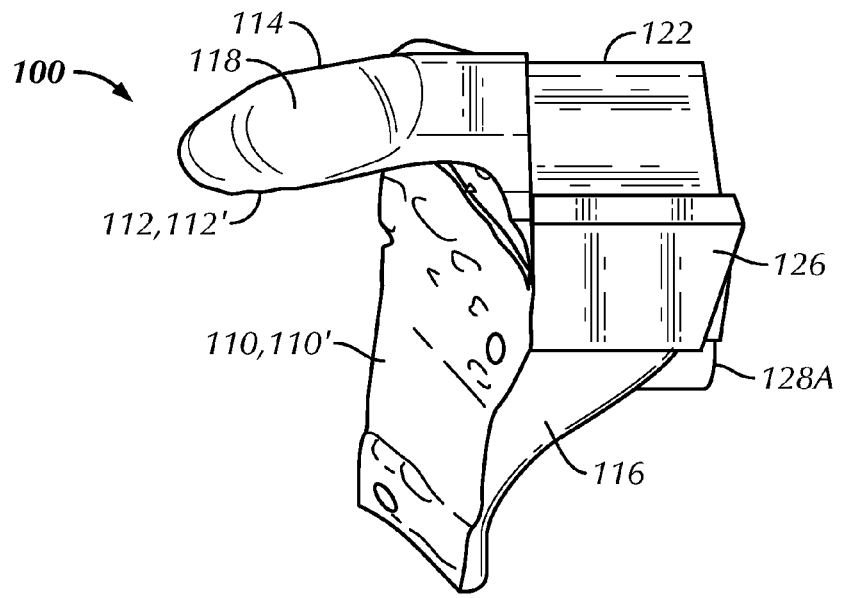
FIG. 9 is a perspective view of the customized unicompartmental tibial cutting guide of FIG. 2.
Figure 10:
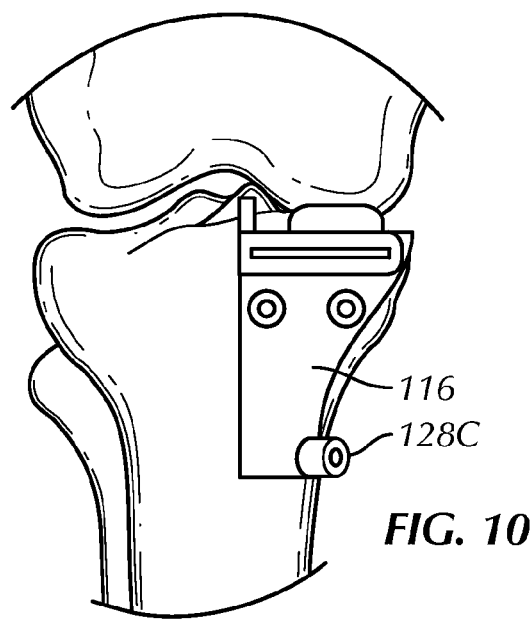
FIG. 10 is a front elevation view of the customized unicompartmental tibial cutting guide of FIG. 2 attached to a tibia of a knee joint.

Substantially opposite the second mating surface is a third surface 118 having a contour for receiving a femoral condyle. For example, as best shown in FIGS. 4, 5 and 9, the third surface is a concave curvature. The third surface 118 is configured to receive and provide a degree of congruence with a distal femoral condyle e.g., when the knee is moved through a full range of motion, when the tibial cutting guide positioned to the tibia, as shown in FIGS. 13 and 14. In general, the negative contour of the third surface is substantially concave in shape.

Thus, as a result of the first and second mating surfaces 110, 112, a user can easily and accurately position the tibial cutting guide 110 in the proper position on the patient's tibia by complementarily aligning the tibia cutting guide with the patient's tibia by way of the patient's tibial bone's natural contours.

Referring back to FIG. 2, the tibial cutting guide 100 also includes a first cutting guide surface 120 positioned distal to the second mating surface 112. The second mating surface is positioned about a proximal end of the tibial cutting guide. Preferably, the first cutting guide surface 120 is provided by a captured cutting block 122 having a slot 124 about the proximal end of the tibial cutting guide. As used herein, a captured cutting block is a cutting block having a cutting surface for receiving a saw blade and wherein the saw blade is completely circumferentially surrounded by the cutting block. The slot 124 is preferably sized from about 1.0-1.8 mm and more preferably about 1.4 mm in height to receive a saw blade, but can alternatively be sized and shaped to receive a variety of cutting tools of varying size. While a captured cutting block may be preferred, the first cutting guide surface can also be provided by an open faced cutting guide surface.

A second cutting guide surface 126 is positioned substantially transverse to the first cutting guide surface 120 and adjacent a medial side of the first mating surface 110. As shown, in FIG. 2, the second cutting guide surface 124 extends vertically from the captured cutting block 122. The second cutting guide surface 124 assists a user in aligning a saw blade for making a vertical cut in the tibia.

Figure 2:
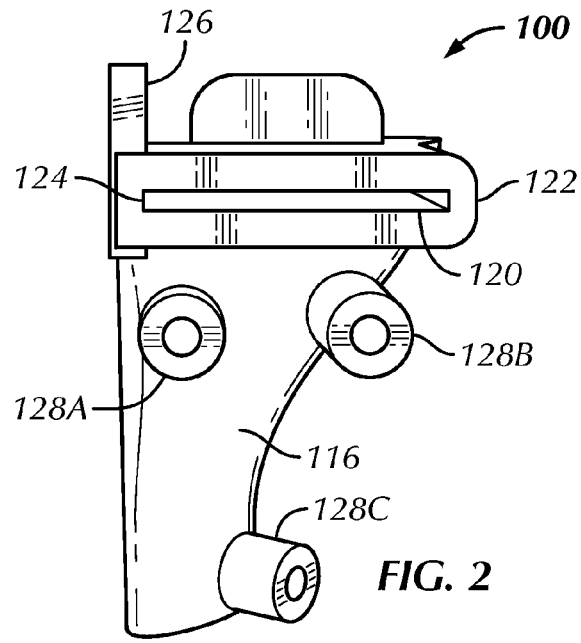
FIG. 2 is a front elevation view of a customized unicompartmental tibial cutting in accordance with a preferred embodiment of the present invention.
Figure 3:
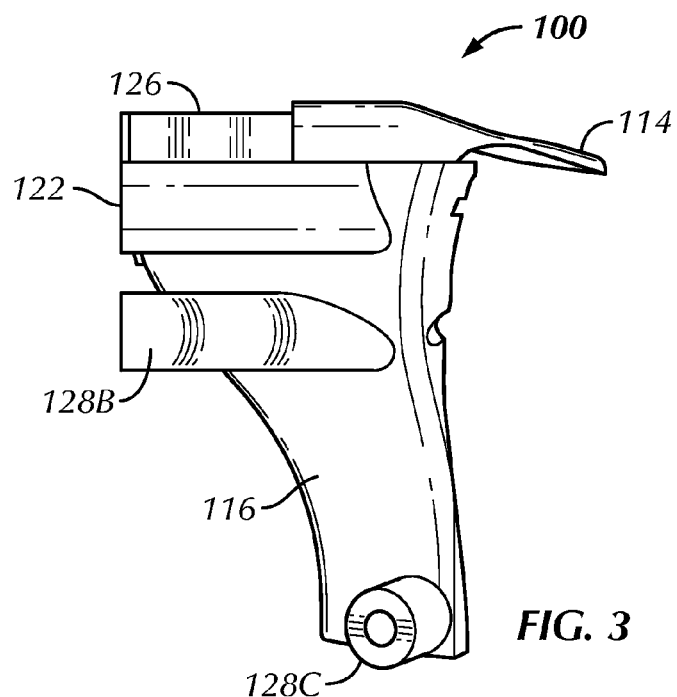
FIG. 3 is a lateral side elevation view of the customized unicompartmental tibial cutting guide of FIG. 2.

Referring to FIGS. 2 and 3, the cutting guide 100 also includes at least two apertures 128A, 128B for receiving fixation pins for securing the cutting guide to the patient's tibia. Preferably, the cutting guide includes a third aperture 128C for receiving a third fixation pin. Each of the apertures 128A-C is arranged on the main body 116 such that their respective longitudinal axes are not co-linear.

The first cutting guide surface 120 can be configured to be perpendicular to a longitudinal axis of the patient's tibia or perpendicular to a mechanical axis of the patient's leg. In addition, referring to FIG. 4, the first mating surface 110 which includes the customized patient-specific negative contour corresponding to the contour of the anterior region of the patient's tibia and the second mating surface 112 can be used to define the longitudinal axis of the patient's tibia or the mechanical axis of the patient's leg thereby aiding in the orientation of the first cutting guide surface 120.

Alternatively expressed, referring to FIG. 4, the customized unicompartmental tibia cutting guide 100 includes a mating surface having a customized patient-specific negative contour to match a corresponding contour of a tibia of the patient extending continuously from a tibial plateau of a medial condyle or a lateral condyle of the tibia to an anterior region of the tibia. The mating surface has a first portion 110' extending along the anterior region of the tibia and continuously to a second portion 112' extending substantially transverse to the first portion to about a midpoint of the tibial plateau of the medial condyle or the lateral condyle of the tibia. The second portion 112' also includes a surface having a concave contour to receive a femoral condyle. Due to the configuration and sizing of the second portion 112', it is limited to a region between and intercondyloid eminence and a lateral or medial edge of the tibial plateau.

The tibia cutting guide 100 also includes a first cutting guide surface 120 and a second cutting guide surface 126. The first cutting guide surface 120 is positioned distal to the second portion 112'. The second cutting guide surface 126 is positioned substantially transverse to the first cutting guide surface and adjacent a medial side of the customized unicompartmental tibial cutting guide.

Figure 15:
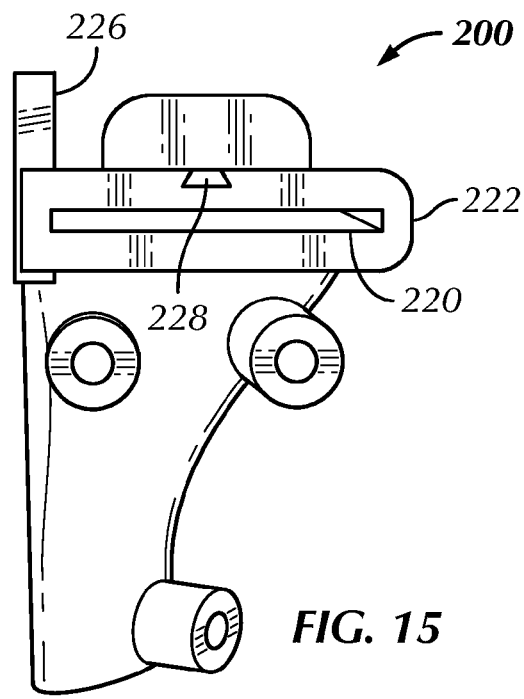
FIG. 15 is a front elevation view of a customized unicompartmental tibial cutting guide in accordance with another preferred embodiment of the present invention.
Figure 16:
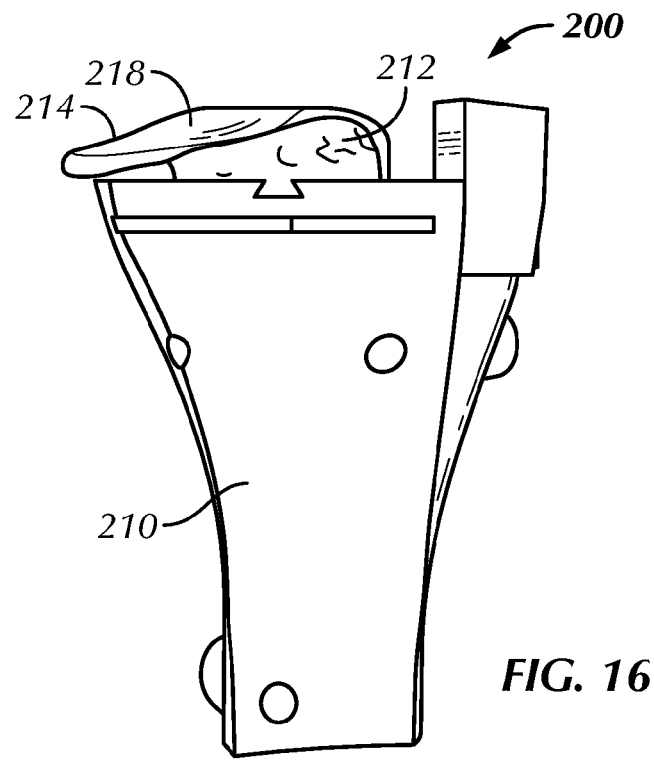
FIG. 16 is a rear perspective view of the customized unicompartmental tibial cutting guide of FIG. 15.

In accordance with another preferred embodiment, the present invention provides a customized unicompartmental tibial cutting guide 200, as shown in FIGS. 15 and 16. The tibial cutting guide 200 is substantially the same as tibial cutting guide 100 and for purposes of brevity, only those features that differ from those of tibial cutting guide 100 will be described hereinafter.

The tibial cutting guide 200 includes a cutting block 222 having a first surface 210 for engagement with an anterior region of a patient's tibia. Unlike tibial cutting guide 100, the first surface 210 of tibial cutting guide 200 is not customized to be a patient-specific negative contour of the tibia. Instead, the cutting block 222 is configured as a uniform cutting block applicable to any tibia. Additionally, the tibial cutting guide 200 includes a first cutting guide surface 220 that extends completely across the cutting block 222 so as to receive e.g., a saw blade. The first cutting guide surface 220 can be provided by way of a captured cutting block or an open faced cutting guide.

The tibial cutting guide 200 further includes a tongue 214 that is recently attachable to the cutting block 222. For example, the tongue 214 can be releasably attachable to the cutting block by way of a dovetail connection 228. Of course, any other connection mechanism readily known in the art can be applicable for connecting the tongue to the cutting block e.g., a tapered dovetail connection, tongue and groove mechanism, snap-fit, or fastener.

The tongue 214 (whish is similar to the tongue 114) includes a mating surface 212 having a customized patient-specific negative contour to match a corresponding contour of a mid-region of one of a tibial plateau of a medial condyle or a tibial plateau of the tibia of the patient. When connected to the cutting block 222, the tongue 214 extends posteriorly from the cutting block a distance sufficient to reach a midpoint of the tibial plateau of the medial condyle or the lateral condyle of the tibia. Preferably, the tongue 214 extends sufficiently posteriorly to reach and terminate at a lowest position of the tibial plateau. As a result of terminating at the lowest position of the tibial plateau, the tongue in combination with the remainder of the tibial cutting guide functions in a clamp-like manner. The width of the tongue 214 is narrower than the cutting block and sized to be situated between the intercondyloid eminence and a lateral or medial edge of tibial plateau. As such, the second mating surface 212 is limited to a region between the intercondyloid eminence and one of the lateral or medial edge of the tibial plateau.

Additionally, similar to tibial cutting guide 100, the tibial cutting guide 200 includes a second cutting guide surface 226 positioned substantially transverse to the first cutting guide surface and adjacent a medial side of the cutting block 222 and a femoral mating surface 218 having a concave contour to receive a femoral condyle.

Thus, the tibial cutting guide 200 having only a tongue 214 that is required to be formed as a patient-specific apparatus advantageously allows for easier manufacturing, reduced cost and utilization of a single uniform base cutting block.

It will be appreciated by those skilled in the art that changes could be made to the embodiments described above without departing from the broad inventive concept thereof. It is to be understood, therefore, that this invention is not limited to the particular embodiments disclosed, but it is intended to cover modifications within the spirit and scope of the present invention as defined by the appended claims.

We claim:

1. A customized unicompartmental tibial cutting guide for orthopedic surgery comprising:
    a cutting block that includes:
        a first surface configured to engage with an anterior region of a tibia, and
        a first cutting guide surface extending across the cutting block; and
    a tongue including a mating surface having a customized patient-specific negative contour to match a corresponding contour of a mid-region of one of a tibial plateau of a medial condyle or a tibial plateau of a lateral condyle of a tibia of a patient, and a concave contour extending from a top surface of the tongue for receiving a femoral condyle.

2. The customized unicompartmental tibial cutting guide of claim 1, wherein the tongue is configured to extend to about a midpoint of the tibial plateau of the medial condyle or lateral condyle when the tibial cutting guide is engaged with the tibia.

3. The customized unicompartmental tibial cutting guide of claim 1, wherein the tongue has a width configured to extend between an intercondyloid eminence and a lateral or a medial edge of the tibial plateau when the tibial cutting guide is engaged with the tibia.

4. The customized unicompartmental tibial cutting guide of claim 1, wherein the cutting block further includes a second cutting guide surface positioned substantially transverse to the first cutting guide surface and adjacent a medial side of the cutting block.

5. The customized unicompartmental tibial cutting guide of claim 1, wherein the tongue is configured to extend to and terminate at a lowest position of the tibial plateau when the tibial cutting guide is engaged with the tibia.

6. A customized unicompartmental tibial cutting guide for orthopedic surgery comprising:
    a cutting block that includes:
        a first surface for engagement with an anterior region of a tibia, and
        a first cutting guide surface extending across the cutting block; and
    a tongue attachable to the cutting block, the tongue including a mating surface having a customized patient-specific negative contour to match a corresponding contour of a mid-region of one of a tibial plateau of a medial condyle or a tibial plateau of a lateral condyle of a tibia of a patient,
    wherein the tongue includes a femoral mating surface having a concave contour to receive a femoral condyle.

7. A customized unicompartmental tibial cutting guide for orthopedic surgery comprising:
    a first mating surface including a customized patient-specific negative contour to match a corresponding contour of an anterior region of a tibia of a patient;
    a tongue extending substantially transverse to the first mating surface to about a midpoint of a tibial plateau of a medial condyle or a lateral condyle of the tibia when the tibial cutting guide is engaged with the tibia, wherein the tongue includes:
        a second mating surface extending along a bottom of the tongue and including a customized patient-specific negative contour to match a corresponding contour of a mid-region of one of the tibial plateau of the medial condyle or the tibial plateau of the lateral condyle, and
        a third mating surface extending along a top surface of the tongue and having a concave contour extending from the top surface to receive a femoral condyle;
    a first cutting guide surface positioned distal to the second mating surface; and
    a second cutting guide surface positioned substantially transverse to the first cutting guide surface and adjacent a medial side of the first mating surface.

8. The customized unicompartmental tibial cutting guide of claim 7, further comprising at least two apertures for receiving fixation pins for securing the cutting guide to the tibia.

9. The customized unicompartmental tibial cutting guide of claim 7, wherein the first cutting guide surface is provided by a captured cutting block.

10. The customized unicompartmental tibial cutting guide of claim 7, wherein the first cutting guide surface is configured to be perpendicular to a mechanical axis of a leg of the patient or configured to be perpendicular to a longitudinal axis of the tibia when the tibial cutting guide is engaged with the tibia.

11. The customized unicompartmental tibial cutting guide of claim 7, wherein the concave contour is shaped to a femoral condyle.

12. The customized unicompartmental tibial cutting guide of claim 7, wherein the second mating surface is configured to terminate at a lowest position of a tibial plateau when the tibial cutting guide is engaged with tibia.

13. The customized unicompartmental tibial cutting guide of claim 7, wherein the second cutting guide surface intersects a plane of the first cutting guide surface.

14. A customized unicompartmental tibial cutting guide for orthopedic surgery comprising:
    a mating surface including a customized patient-specific negative contour to match a corresponding contour of a tibia of a patient and extending continuously from a tibial plateau of a medial condyle or a lateral condyle of the tibia to an anterior region of the tibia when the tibial cutting guide is engaged with the tibia, wherein the mating surface includes:
        a first portion for extending along the anterior region of the tibia, and
        a second portion extending continuously from and substantially transverse to the first portion and configured to extend to about a midpoint of the tibial plateau of the medial condyle or the lateral condyle of the tibia when the tibial cutting guide is engaged with the tibia,
        wherein the second portion has a top surface spaced from the first portion having a concave contour extending from the top surface to receive a femoral condyle;
    a first cutting guide surface positioned distal to the second portion; and
    a second cutting guide surface positioned substantially transverse to the first cutting guide surface and adjacent a medial side of the customized unicompartmental tibial cutting guide.

15. The customized unicompartmental tibial cutting guide of claim 14, further comprising at least two apertures for receiving fixation pins for securing the cutting guide to the tibia.

16. The customized unicompartmental tibial cutting guide of claim 14, wherein the first cutting guide surface is provided by a captured cutting block slot.

17. The customized unicompartmental tibial cutting guide of claim 14, wherein the first cutting guide surface is configured to be perpendicular to a mechanical axis of a leg of the patient or configured to be perpendicular to a longitudinal axis of the tibia when the tibial cutting guide is engaged with the tibia.

18. The customized unicompartmental tibial cutting guide of claim 14, wherein the top surface having the concave contour is shaped to a femoral condyle.

19. The customized unicompartmental tibial cutting guide of claim 14, wherein the second portion is configured to terminate at a lowest position of the tibial plateau when the tibial cutting guide is engaged with the tibia.

20. The customized unicompartmental tibial cutting guide of claim 14, wherein the second cutting guide surface intersects a plane of the first cutting guide surface.

* * * * *